United States Patent
Kermani

(10) Patent No.: US 7,467,117 B2
(45) Date of Patent: Dec. 16, 2008

(54) ARTIFICIAL INTELLIGENCE AND GLOBAL NORMALIZATION METHODS FOR GENOTYPING

(75) Inventor: Bahram Ghaffarzadeh Kermani, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

(21) Appl. No.: 11/270,227

(22) Filed: Nov. 8, 2005

(65) Prior Publication Data

US 2006/0224529 A1 Oct. 5, 2006

Related U.S. Application Data

(62) Division of application No. 10/809,608, filed on Mar. 24, 2004, now Pat. No. 7,035,740.

(51) Int. Cl.
*G06F 15/18* (2006.01)

(52) U.S. Cl. .............................. 706/20; 706/16; 706/15

(58) Field of Classification Search .................. 706/20, 706/16, 15; 707/6
See application file for complete search history.

(56) References Cited

U.S. PATENT DOCUMENTS

| | | | |
|---|---|---|---|
| 4,697,242 A | 9/1987 | Holland et al. | |
| 4,935,877 A | 6/1990 | Koza | |
| 5,526,281 A | 6/1996 | Chapman et al. | |
| 6,228,593 B1 | 5/2001 | Lipshutz et al. | |
| 6,326,147 B1 | 12/2001 | Oldham et al. | |
| 6,584,410 B2 | 6/2003 | Berno | |
| 6,925,389 B2* | 8/2005 | Hitt et al. ...................... | 702/19 |
| 7,035,739 B2* | 4/2006 | Schadt et al. .................. | 702/19 |
| 7,107,155 B2* | 9/2006 | Frudakis ....................... | 702/19 |
| 2002/0059154 A1* | 5/2002 | Rodvold ........................ | 706/26 |
| 2003/0204320 A1* | 10/2003 | Arouh et al. ................... | 702/20 |
| 2004/0030503 A1* | 2/2004 | Arouh et al. ................... | 702/20 |

FOREIGN PATENT DOCUMENTS

WO   WO-2004/003234 A2   1/2004

OTHER PUBLICATIONS

Dunagan, J. et al., "Optimal Outlier Removal in High-Dimensional Spaces," MIT Laboratory for Computer Science, 317-318 (2003).
Fan, J-B. et al., "Highly Parallel SNP Genotyping," Cold Springs Harbor Symposia on Quantitative Biology, LXVIII:69-78 (2004).
Hill, A. et al., "Evaluation of normalization procedures for oligonucleotide array data on spiked cRNA controls," Genome Biology, 2(12):1-13(2001).
Kermani, B.G. et al., "A New Method in Obtaining a Better Generalization in Artificial Neural Networks," Proceedings of the 16th Annual International Conference of the IEEE Engineering in Medicine and Biology Society, 482:2, November, Baltimore, Maryland (1994).

(Continued)

*Primary Examiner*—Joseph P. Hirl
*Assistant Examiner*—Adrian L Kennedy
(74) *Attorney, Agent, or Firm*—Calvin Fan; John T. Murphy

(57) ABSTRACT

Described herein are systems and methods for normalizing data without the use of external controls. Also described herein are systems and methods for analyzing cluster data, such as genotyping data, using an artificial neural network.

20 Claims, 10 Drawing Sheets

OTHER PUBLICATIONS

Liu, W-M. et al., "Algorithms for large-scale genotyping microarrays," Bioinformatics, 19:2397-2403 (2003).

Shen, R. et al., "Optimization of Production-Scale Genotyping Assay Tutorial: High-Multiplex SNP Genotyping Assay Benefits from Integration With a Turnkey Production System," Genetic Engineering News, 23: (2003).

Tsukii, K. et al., "Development of an Automated SNP Analyzer," Furukawa Review, 24:88-93 (2003).

Wang, E. et al., "A strategy for detection of known and unknown SNP using a minimum number of oligonucleotides applicable in the clinical setting," Journal of Translational Medicine, 1:1-14 (page number not for citation purposes) (2003).

* cited by examiner

ARTIFICIAL INTELLIGENCE AND GLOBAL NORMALIZATION METHODS FOR GENOTYPING

This application is a divisional of U.S. patent application Ser. No. 10/809,608, filed on Mar. 24, 2004, now U.S. Pat. No. 7,035,740 now allowed, which is incorporated herein by reference.

FIELD OF THE INVENTION

The invention described herein relates to the fields of computer science, machine learning, artificial intelligence, pattern recognition, bioinformatics and bioinformation processing. More specifically, the present invention relates to data analysis using artificial neural networks. Even more specifically, the present invention relates to genotyping via supervised training.

BACKGROUND

Recent advances in the field of miniaturization have led to an increase in the speed and efficiency of high-throughput molecular assays. However, when such high-throughput technology is used, manual data analysis is rarely feasible in view of the large number of samples that can be processed during a single experiment. As such, computers play a central role in both the processing and analysis of data generated from high throughput experiments.

One area where miniaturization has had a profound effect is in the field of nucleic acid research. In particular, improvements in microarray technology and other comparable high-throughput systems have facilitated vast increases the number of nucleic acid samples that can be simultaneously processed. The field of genotyping has particularly benefited from miniaturization technology.

Genotyping is a branch of nucleic acid research in which a set of genetic markers (loci) in an individual are analyzed to determine the individual's genetic composition. In humans and other organisms, the nucleotide sequence of each genetic locus is largely identical between individuals. However, in some loci there exists one or more portions of nucleotides which exhibit some variation between individuals. Two variants of the same genetic locus are referred to as alleles. The most common type of genetic variation among humans and other organisms is the single nucleotide polymorphism (SNP). A SNP is a single nucleotide variation among individuals in a population that occurs at a specific nucleotide position within a locus. In humans, about 1.42 million SNPs are estimated to be distributed throughout the genome and at least 60,000 of these SNPs are thought to be in the coding portions of genes (The International SNP Map Working Group (2001) Nature 409:928-933). Determining whether an individual possesses one or more of these SNPs can be used to, among other things, determine that individual's risk of having certain diseases as well as determine that individual's relationship to other individuals. Microarray technology permits the analysis of thousands of specific genetic markers from multiple individuals all on a single device.

Due to the large number of DNA samples that are processed using high-throughput technology, automated systems have been heavily utilized to perform many facets of genotyping analyses, including genotype clustering and identification. In such systems where genotyping is automated, it is of paramount importance to have reproducible clusters reflecting whether individuals are homozygous or heterozygous for a particular allele. Depending on the analytical methods used, factors such as, intensity changes, cross-talk between channels, and intensity offsets, if left untreated, can alter the location of genotype clusters, and thereby skew the results of the genotyping analysis. Accordingly, practitioners have used several methods to compensate for factors that affect the proper clustering of genotypes from a genotyped data set.

One way in which variation from experimental factors is treated is by normalizing raw genotype data based on a set of external control samples. However, such methods rely on the assumption that the nature of the controls do not change from sample to sample. Because this assumption is not usually true, normalization with external controls provides only a marginally effective means to limit data variation. Furthermore, on occasion normalizing using external controls can deteriorate the quality of the data. As such, there is need to provide an improved method for normalizing genotyping data.

Another issue associated with automated genotyping systems is that highly accurate genotype calling is not always achieved. For example, one way to evaluate genotype data is by comparing the signal intensity of one allele against another. After normalization, the data points are typically subjected to some form of cluster analysis whereby the data set is divided into specific regions (clusters) each of which are assigned to a specific genotype. However, very few robust methods of accurate genotype clustering currently exist. Problems are often due to the fact that certain alleles occur at low frequencies and because biological samples are not necessarily representative of a natural population. As such, it is often times difficult to identify whether a particular genotype is represented in the data set (i.e., determine whether one or more clusters are missing), and if not present, where a missing genotype would lie in relation to other genotypes (i.e., predict the location of missing clusters). In cluster-based genotype analysis, improving cluster identification greatly improves the accuracy of genotype calls. Accordingly, there is a need for improved methods of analyzing genotyping data to accurately define, and if necessary, predict genotype clusters.

SUMMARY OF THE INVENTION

Some embodiments of the present invention relate to overcoming or alleviating difficulties and/or deficiencies that are associated with methods of data analysis such as genetic analysis.

Another embodiment of the present invention relates to improving or replacing certain currently used methods for normalizing data.

Further embodiments of the present invention relate to methods and systems for normalizing data without the use of external controls. In such embodiments, the data is normalized by selecting points within the actual data set as a reference then transforming the entire data set such that all of the data points are normalized with respect to each other. In certain embodiments of the present invention, the data that is normalized is genotyping data.

Another embodiment of the present invention relates to improving certain currently used methods for evaluating data by cluster-based data analysis.

Further embodiments of the present invention relate to systems and methods for genotyping using an artificial neural network. In some genotyping embodiments, an artificial neural network is employed in determining genotype clusters (cluster determination). In other genotyping embodiments, an artificial neural network is employed in computing the probability of a biological sample having a particular genotype (score computation). In still other embodiments, an artificial neural network is used for cluster determination and score computation.

DETAILED DESCRIPTION

Figure 1:
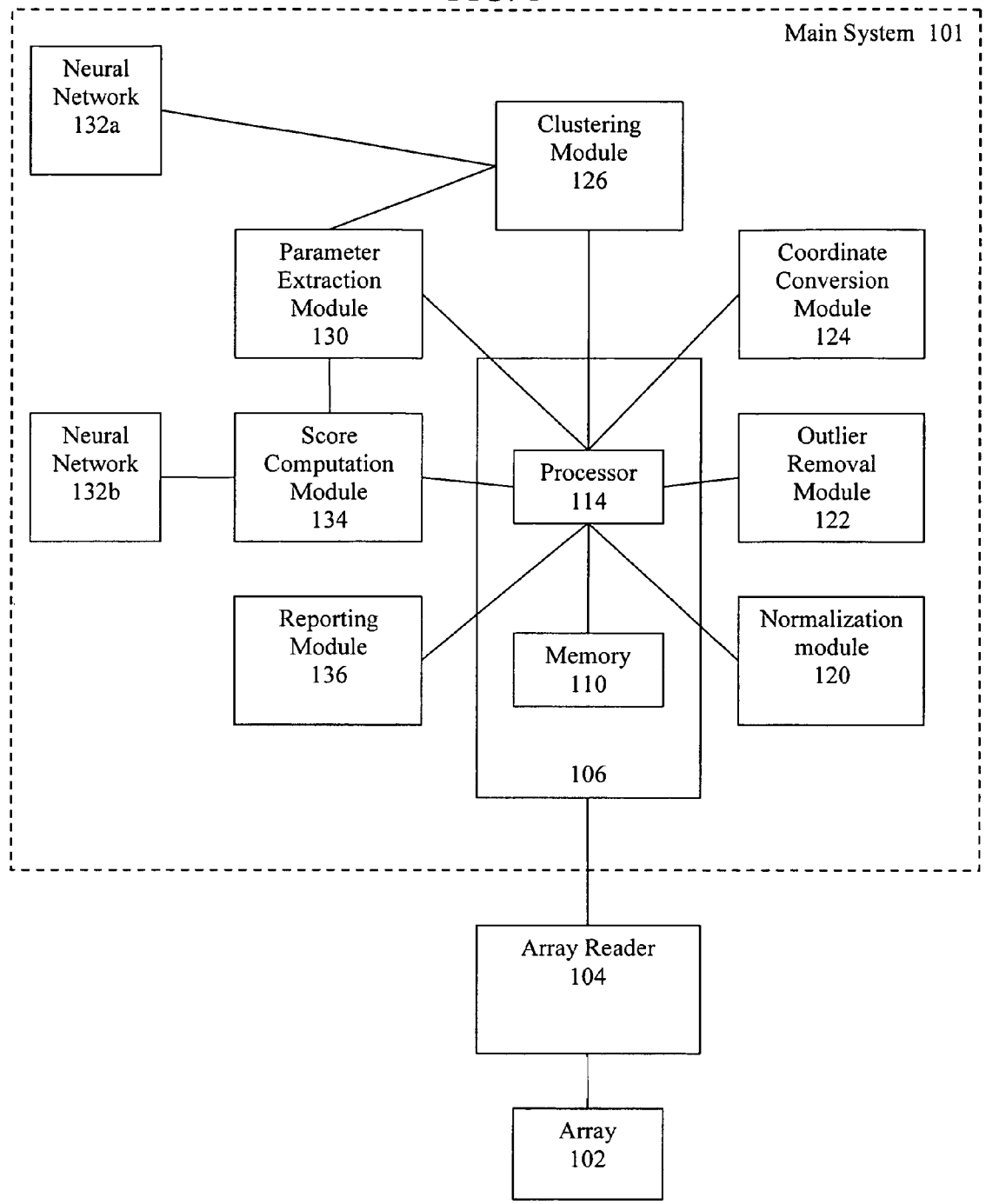
FIG. 1 is a schematic diagram representing a system for genetic analysis.

Some embodiments of the present invention relate to methods and systems for analyzing cluster data using an artificial neural network. Many of the methods described herein permit rapid supervised and/or unsupervised training of the neural network so as to achieve rapid and accurate analysis of the input data.

Some embodiments of the present invention relate to methods and systems for genotyping using an artificial neural network. In such embodiments, more than one artificial neural network may be used for particular genotyping tasks. For example, an artificial neural network can be used to determine whether certain genotype clusters are missing from a data set. If one or more genotype clusters are missing, the neural network can be used to predict the location of the missing cluster and to define its boundaries as a function of probability. Artificial neural networks can also be used to assign genotyping data, which is obtained from the analysis of a biological sample, to appropriate genotype clusters.

Embodiments of the present invention also relate to normalizing data without using external controls. In such embodiments, actual data from the data set is used to generate a reference data set. The entire data set can then be transformed with respect to the internally generated reference set.

It will be appreciated that the artificial neural network-based cluster analysis processes and systems described herein, and the normalization methods can be applied to many different types of cluster data which includes, but is not limited to, genotyping data, gene expression data, data from case control studies or quality control data.

DEFINITIONS

As used herein, the term "genetic data" is intended to mean information correlating at least one signal with the presence or amount of a nucleotide sequence in a cell. Exemplary genetic data includes, without limitation, data from a genotyping assay, mutation detection assay, gene expression assay or the like. Exemplary signals include, without limitation, a signal from a labeled probe used to detect a nucleotide sequence such as a fluorescent or luminescent signal or an electronic signal stored in a computer readable memory.

As used herein, the term "locus" is intended to mean the position of a marker in a nucleic acid sequence. The nucleic acid sequence can be a sequence of a molecule such as a chromosome. The nucleic acid sequence can also be a sequence in a database such as a genome sequence and can be a particular build or version of a genome sequence. The term is intended to encompass positions on a nucleic acid expressed or otherwise derived from a source genomic DNA, wherein the position can be determined on the source genomic DNA. Exemplary markers encompassed by the term include, but are not limited to, genes, single nucleotide polymorphisms (SNPs), mutations, nucleotide sequences of defined composition and/or length, introns, exons, or restriction sites.

As used herein, the term "allele" is intended to mean one of two or more alternative forms of a marker at a locus. The invention can be used for analysis of loci having two alleles (bi-allelic loci) or loci having higher numbers of alleles including, for example, 3 alleles, 4 alleles or 5 alleles. Typically, an allele is associated with a particular trait such as a phenotype. A plurality of alleles can constitute a genotype. A genotype can include, for example, at least about 2, 5, 10, 50, 100, 500, 1000, 10,000 or more alleles As used herein, the term "coordinate system" is intended to mean a representation relating points in a space of given dimensions. A representation included in the term can be in a graphical format. However, the representation need not be graphical and can be any of a variety of other known formats including, for example, a table or format used in computer readable memory. Exemplary coordinates useful in the invention include, without limitation, Cartesian coordinates or polar coordinates. Dimensions useful in a coordinate system of the invention can include, for example, a linear, log (base 2, 10, e or others), Box-Cox, square-root or arc tangent scale.

As used herein, the term "signal value" is intended to mean a number correlating the level of a detected molecule with a detected characteristic of the molecule. A level of a detected molecule can be binary such that the signal value indicates presence or absence of the detected molecule, for example, without indicating the amount of the molecule that is present. Alternatively, the level can correlate with the amount of molecule detected such as a signal intensity value. A signal value can be represented as a point in a coordinate system. A signal value can be included in a signal value scatter point having coordinates corresponding to signal values for 2 or more alleles when plotted in a scatter plot having axes corresponding to signal values for the two or more alleles.

As used herein, the term "sweep points" is intended to mean a set of points that are spaced according to a defined function along a line or curve. The line can be an axis of a coordinate system. Alternatively the line can cross through the origin of a coordinate system at a desired angle including, for example, a 30°, 45° or 60° angle.

As used herein, the term "control point" is intended to mean a signal value upon which normalization is based. A control point &an be a signal value that is closest to a particular sweep point in a set of signal values.

As used herein, the term "set point" is intended to mean the location on a line to which a control point is transferred when determining parameters of a registration transformation equation. The location to which a set point is transferred can be, for example, on an axis of a coordinate system.

As used herein, the term "cluster" is intended to mean a plurality of individual entities grouped together according to at least one similar property. Exemplary similar properties that can be used to group entities include, without limitation, proximity when related in a given coordinate system or presence of at least one of the same alleles. A further similar property for a plurality of entities can be common exclusion of those entities from a second cluster or cluster location.

As used herein, the term "location," when used in reference to a cluster, is intended to mean a portion of a coordinate system that specifies points that are or should be included in the cluster. A location for a missing cluster can be specified, for example, according to the coordinates or limits specifying points that would be present in the cluster whether the points are present in a plot or not. Inclusion of points in a cluster can be specified, for example, by a probability function. Thus, a location can be, but need not be, defined by an absolute boundary or limit.

As used herein, the term "cluster model" is intended to mean a representation of spatial or relational limits for members of a group in a coordinate system. Spatial limits in a coordinate system can include, for example, one or more coordinates specifying an area of inclusion or exclusion, one or more coordinates specifying a maximum value or minimum value, or a probability that one or more coordinates do or do not belong to a particular group. A relational limit in a coordinate system can include, for example, a distance between two points, the absolute location of points, the context-dependent position of points, or the distance or similarity between groups of two or more points (e.g., Mahalanobis distance).

As used herein, the term "fit," when used in reference to a cluster model and genetic data, is intended to mean a measure of the extent to which the cluster model accurately groups the data into at least one cluster.

As used herein, the term "best fit," when used in reference to a cluster model and genetic data, is intended to mean a cluster model that groups the genetic data into at least one cluster more accurately than at least one other cluster model.

Description of Particular Embodiments

The invention provides a genotyping system. The system can include one or more of the following (a) an array reader configured to detect signals from separate locations on an array substrate; (b) a computer processor configured to receive signal values from the array reader; (c) a normalization module including commands for (i) reading the signal values; (ii) identifying a set of sweep points for the signal values in a coordinate system; (iii) identifying a set of control points, the control points including at least a subset of the signal values that are proximal to the sweep points; (iv) determining parameters of a registration transformation equation based on the control points; and (v) transforming the signal values according to the registration transformation equation and the parameters, thereby providing normalized genetic data; and (d) a clustering module including commands for (i) reading the normalized genetic data; (ii) comparing fit of the normalized genetic data to each of a plurality of cluster models using an artificial neural network, thereby determining a best fit cluster model; and (iii) assigning the signal values to at least one cluster according to the best fit cluster model, wherein if the best fit cluster model contains at least one actual cluster and at least one missing cluster, then using a second artificial neural network to propose a location for the at least one missing cluster.

FIG. 1 depicts an exemplary genetic analysis system 100 which comprises a main system 101 which is coupled to one or more devices that are involved in sample detection and/or identification. In FIG. 1, the main system 101 is coupled to an array reader 104 which is configured to detect signals from an array 102 which contains one or more nucleic acids. Although FIG. 1 specifically exemplifies a system which includes an array and an array reader, it will be appreciated that any other device that is capable of providing genetic data can be coupled to main system 101 including, for example, a database of allele associated signal values or allele levels for loci of an individual or population of individuals.

Main system 101 can include a conventional or general purpose computer system 106 that is programmed with, or otherwise has access to, one or more program modules involved in the analysis of genotyping data. Exemplary computer systems that are useful in the invention include, but are not limited to personal computer systems, such as those based on Intel™, IBM™, or Motorola™ microprocessors; or work stations such as a SPARC™ workstation or UNIX™ workstation. Useful systems include those using the Microsoft™ Windows™, UNIX™ or LINUX™ operating system. The systems and methods described herein can also be implemented to run on client-server systems or wide-area networks such as the Internet.

Computer system 106, which can be configured to operate as either a client or server, can include one or more processors 114 which are coupled to a random access memory (RAM) 110. It will be appreciated that computer system 106 is presented for purposes of illustrating the basic hardware underlying the client and/or server components that can be employed in embodiments of the present invention. Implementation of embodiments of the present invention however, is not limited to any particular environment or device configuration. The embodiments of the present invention may be implemented in any type of computer system or processing environment capable of supporting the methodologies which are presented in further detail below.

Processor 114 can execute the instructions included in one or more program modules. Program modules can be integrated into hardware components of the main system 101, such as firmware encoded on a ROM chip, or may be introduced into the system as separately available software. In particular embodiments, high-level algorithms are written in MATLAB™. Using MATLAB™ Compiler, the MATLAB™ code can be converted automatically to C or C++, and then by calling (transparently) the C compiler, an executable code (machine code) can be generated. If desired the algorithms can be written in a lower level language such as C to begin with. Other computer languages known in the art can be used as well.

In some embodiments, program modules included in main system 101 are selected from: normalization module 120, outlier removal module 122, coordinate conversion module 124, clustering module 126, parameter extraction module 130, score computation module 134 and reporting module 136. Certain program modules such as clustering module 126 and score computation module 134 may incorporate instructions for an artificial neural network (ANN) 132a or 132b which perform some or all of the analysis that is conducted by the module. In some embodiments, a single ANN performs both clustering and score computation functions. In other embodiments, clustering and score computation can be implemented by two or more different ANNs as shown in FIG. 1. Furthermore, in some embodiments, the same ANN can be trained with different training data for use in different steps of the methods disclosed herein.

It will be appreciated that main system 101 need not include all of the above program modules. In some embodiments, only one or a few of the program modules are included in main system 101. It will also be appreciated that the program modules described herein may be combined together or with one or more other modules of different function. Additionally, if desired, the program modules can be further broken down or rearranged so long as main system 101 retains its intended function, such as one or more of the functions set forth in this disclosure.

Figure 2:
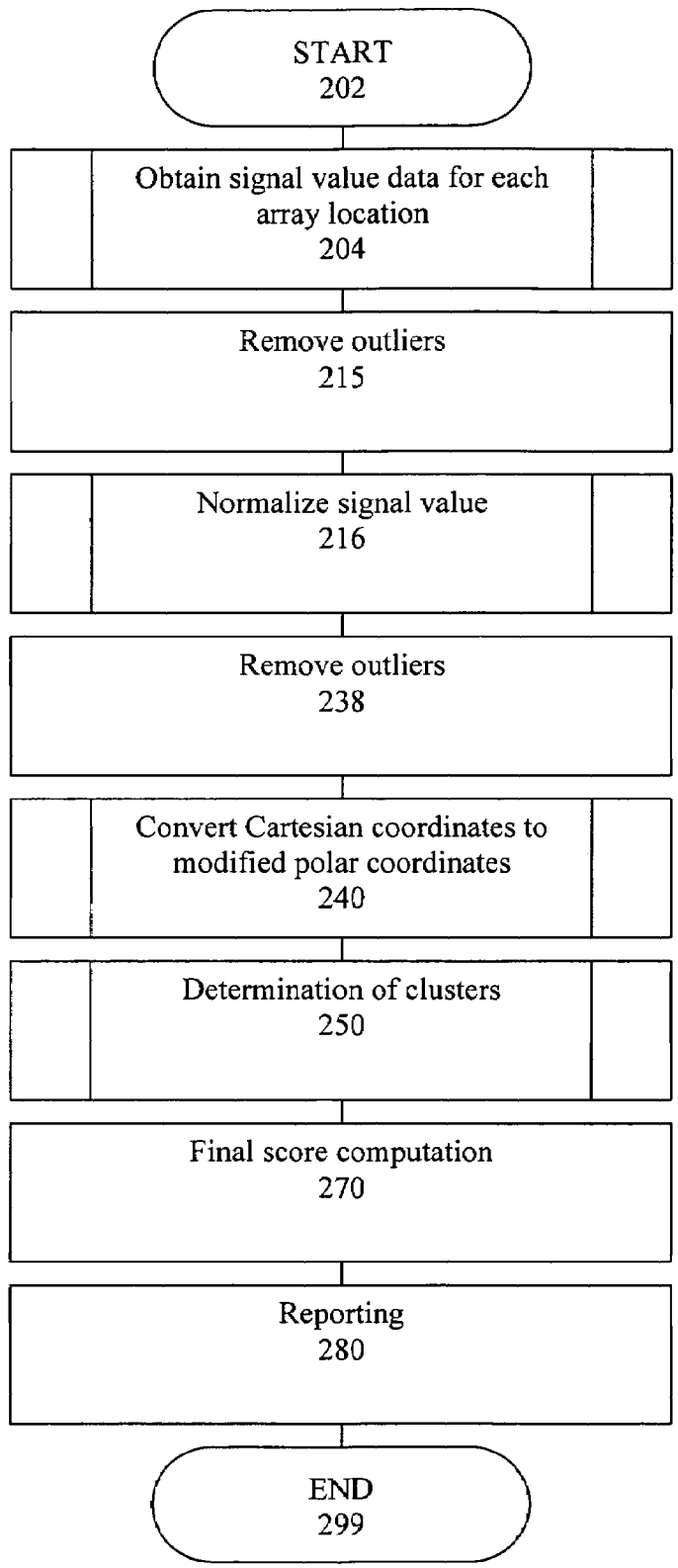
FIG. 2 is flow diagram depicting an overview of a genotyping process.

FIG. 2 is a flow diagram of process 200 by which genotyping data can be analyzed, for example, using the genetic analysis system depicted in FIG. 1. Upon start 202 the genotyping process is executed. In the data acquisition step 204, signal value data can be obtained from a signal generating source or database. Step 204 is explained more completely below with reference to FIG. 3. In some embodiments, the signal generating source is array reader 104 which transmits information such as signal type and signal intensity. Particularly useful array readers include the BeadArray Reader manufactured by Illumina Inc. (San Diego, Calif.). Other known scanners can also be used such as the Axon Scanner (Axon Instruments, Inc., Union City, Calif.).

In outlier removal step 215, outlier signal values are removed from the raw signal value data set. Once outlier signals are removed, the signal values for the entire data set can be normalized in normalization step 216. The normalization step 216 is explained more completely below with reference to FIG. 4.

Subsequent to normalization step 216, a second outlier removal step 238 can optionally be used to remove outlier signal values from the normalized signal value data set. This normalized data can then be converted from a Cartesian data set to modified polar coordinate data in conversion step 240, if desired. The conversion step 240 is explained more completely below with reference to FIG. 5. The modified polar coordinate data can then be subjected to analysis to determine genotype clusters in cluster analysis step 250. This step is explained more completely below with reference to FIG. 6. Subsequent to cluster analysis step 250, final genotyping scores can be computed in score computation step 270. Finally, in step 280, the genotyping scores can be reported to a user via any of a variety of convenient formats including, for example, a graphical user interface or hardcopy printout. The process terminates at an end step 299 when all of the data signals have been processed.

The systems and methods of the invention are exemplified herein with respect to genotyping data for purposes of illustration. Those skilled in the art will recognize that similar methods can be applied to other types of data including, for example, genetic data such as gene expression data or other data obtained from nucleic acid probe arrays and/or multiplexed nucleic acid detection assays.

One of ordinary skill in the art will understand that the processes and systems of the present invention can be implemented for use with various devices and methods that are used to produce genotyping data. An exemplary method involves the use of microarrays and differentially labeled allele-specific nucleic acid probes. Another example, which is described below, is a genotyping system which utilizes fluorescent labels and fiber optics to transmit data signals to the main system 101.

In some embodiments, a method or system of the invention is used to analyze a plurality of genetic loci from one or more individuals detected in a multiplexed assay.

The number of loci used in the invention can be at least 2, 5, 10, 50, 100, 500, 1000, $1\times10^4$, $5\times10^4$, $1\times10^5$, or more up to and including the number of loci in the one or more individuals being evaluated.

Multiplexed genetic analyses can be carried out on an array. An array useful in the invention can be any population of different probe molecules that are attached to one or more substrates such that the different probe molecules can be differentiated from each other according to relative location. Accordingly, in a genetic assay, such as those set forth in further detail below, signals arising from each location are indicative of the levels of particular alleles due to interaction of probes with target allele sequences.

An array can include different probe molecules that are each located at a different addressable location on a substrate. Alternatively, an array can include separate substrates each bearing a different probe molecule, wherein the different probe molecules can be identified according to the locations of the substrates on a surface to which the substrates are attached or according to the locations of the substrates in a liquid. Exemplary arrays in which separate substrates are located on a surface include, without limitation, those having beads in wells as described, for example, in U.S. Pat. No. 6,355,431 B1, U.S.2002/0102578 and PCT Publication No. WO 00/63437. Exemplary formats that can be used in the invention to distinguish beads in a liquid array, for example, using a microfluidic device, such as a fluorescent activated cell sorter (FACS), are described in U.S. Pat. No. 6,524,793. Further examples of arrays that can be used in the invention include, without limitation, those described in Butte, Nature Reviews Drug Discov. 1:951-60 (2002) or U.S. Pat Nos. 5,429,807; 5,436,327; 5,561,071; 5,583,211; 5,658,734; 5,837,858; 5,874,219; 5,919,523; 6,136,269; 6,287,768; 6,287,776; 6,288,220; 6,297,006; 6,291,193; 6,346,413; 6,416,949; 6,482,591; 6,514,751 and 6,610,482; and WO 93/17126; WO 95/11995; WO 95/35505; EP 742 287; and EP 799 897.

An exemplary high density array that can be used is an array of arrays or a composite array having a plurality of individual arrays that is configured to allow processing of multiple samples. Such arrays allow multiplex detection of large pluralities of target loci and/or interrogation of large populations of probes. Exemplary composite arrays that can be used in the invention are described in U.S. Pat. No. 6,429,027 and U.S. 2002/0102578. In particular embodiments, each individual array can be present within each well of a microtiter plate by attachment to the well or temporary introduction to the well. Thus, depending on the size of the microtiter plate and the size of the individual array, very high numbers of assays can be run simultaneously; for example, using individual arrays of 2,000 probes and a 96 well microtiter plate, 192,000 assays can be performed in parallel; the same number of probes in each well of a 384 microtiter plate yields 768,000 simultaneous assays, and in a 1536 microtiter plate gives 3,072,000 assays.

An array useful in the invention can be made by any of a variety of methods known in the art. In a particular embodiment, the surface of a substrate can be modified to contain chemically modified sites that are useful for attaching, either covalently or non-covalently, probe molecules or particles having attached probe molecules. Alternatively, nucleic acid probes can be attached by sequential addition of nucleotide units to synthesize the nucleic acid in situ. Exemplary methods of array manufacture include, without limitation, ink-jet printing methods as described, for example, in U.S. Pat. Nos. 5,981,733; 6,001,309; 6,221,653; 6,232,072 or 6,458,583; spotting techniques such as those described in U.S. Pat. No. 6,110,426; photolithographic synthesis methods such as those described in U.S. Pat. Nos. 6,379,895 or 5,856,101; bead assembly methods as described in U.S. Pat. No. 6,429,027 and U.S.2002/0102578 or printing method utilizing a mask as described in U.S. Pat. No. 6,667,394.

Any of a variety of assays can be used to detect alleles or other genetic markers in a method of the invention. In particular embodiments, target nucleic acids bearing markers can be hybridized to probes of an array and signals arising as a result of hybridization detected. In particular embodiments, a marker can be detected based on the presence of a probe, SNP bearing target or both in a hybrid occurring at a particular location of an array, without subsequent modification of the hybrid species. For example, a pre-labeled gDNA fragment having a particular SNP (indicative of a particular allele) can be identified based on presence of the label at a particular array location where a probe nucleic acid complementing the SNP resides.

In particular embodiments, arrayed nucleic acid probes can be modified while hybridized to target nucleic acids, thereby allowing detection. Such embodiments include, for example, those utilizing allele-specific oligonucleotide hybridization, allele-specific primer extension (ASPE), single base extension (SBE), oligonucleotide ligation amplification (OLA), rolling circle amplification (RCA), extension ligation (GoldenGate™), invader technology, probe cleavage or pyrosequencing as described in U.S. Pat. No. 6,355,431 B1 or U.S. Ser. No. 10/177,727.

The GoldenGate™ assay can be carried out as described in Shen et al., *Genetic Engineering News* 23 (2003). Briefly, samples of DNA are obtained from one or more individuals. Target loci within the DNA samples are contacted with probe sets having three probes each. Probes included in each set are a single locus-specific oligonucleotide probe (LSO) having a universal tag sequence, and first and second allele-specific oligonucleotide probes (ASO), each ASO being specific for one of two possible alleles at the locus. The ASO that is complementary to the allele present at the target locus will anneal on the same strand as the LSO probe such that a gap is present between the annealed LSO and ASO. A polymerase and ligase are added such that the gap is filled and a ligated LSO-ASO probe is produced. The ligated LSO-ASO probe can then be amplified by polymerase chain reaction (PCR), and the amplicons captured by a probe array via the Universal tag on the LSO. The identity of which ASO is ligated to the captured LSO can be identified according to the presence of one of two labels. Thus, the intensity of fluorescence emitted at a first and second wavelength for each array location can be detected and correlated with the levels of the first and second alleles in the sample being tested The probe ligation, PCR amplification and array detection steps can be carried out at a high level of multiplex, thus permitting the simultaneous analysis of thousands of different loci in a single sample of genomic DNA.

Figure 3:
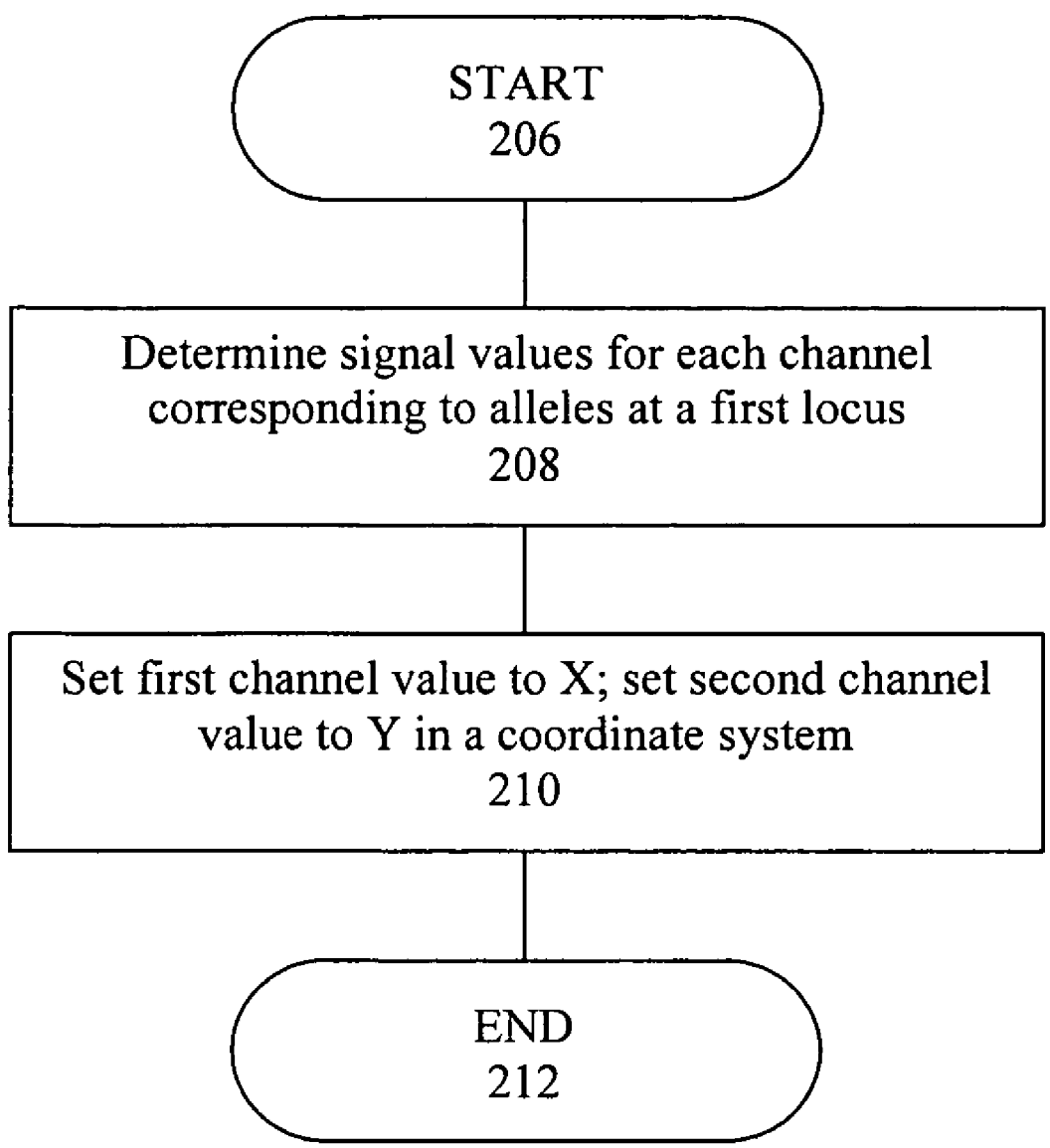
FIG. 3 is a flow diagram depicting a process of data signal acquisition.

In the above-exemplified GoldenGate™ assay the dye-labeled amplified ligated probe products can bind to array 102 in a locus-specific manner to a locus-specific address oligonucleotide that is present in a plurality of copies attached to a microbead that is deposited on a substrate. Emissions characteristic of the fluorescent label are transmitted from each bead to array reader 104 which converts the fluorescent emissions to signals each having an intensity at wavelength 1 (channel 1) and wavelength 2 (channel 2). Similarly, signals can be measured from specific probes on other types of arrays. FIG. 3 is a flow diagram relating the steps in process 204 in which signal value data corresponding to particular array locations is collected. The first step of the process is signal value determination step 208. Signal values can be determined in accordance with a particular genetic assay being used in the methods such as those set forth previously herein. By way of example, when the GoldenGate™ assay is used, step 208 can be carried out by determining signal intensity for each channel at a single array location. The array location can be for example a fiber of a fiber optic array such as a Sentrix BeadArray (Illumina, Inc. San Diego), described in U.S. Pat. No. 6,429,027 and U.S.2002/0102578 or a bead location on a BeadChip Array (Illumina, Inc. San Diego), described in U.S. Pat. No. 6,429,027 and U.S.2002/0102578. An array location for a probe that is complementary to a specific LSO, can be detected using two different channels such that the signal intensity of a first channel detects a first label corresponding to a first allele at that locus. Similarly, the intensity of the signal read for a second label at a second channel represents a measurement of the frequency of the second allele at the same locus. Those skilled in the art will understand that other formats can be used. For example, first and second alleles can be detected by data channels placed to detect different array locations that bind to different alleles.

The next step shown for process 204 is data set generation step 210 in which the signal values determined from each data channel are plotted as scatter points in a coordinate system. Continuing with the above example of a GoldenGate™ assay, the signal intensity of channel 1 can be set to an x-value that is measured in arbitrary units. Similarly, the intensity of channel 2 can be set to a y-value which is measured in the same arbitrary units as the x-value. The x and y values thereby define the location of a set of first and second signal values on a Cartesian coordinate system, the set of signal values being in the form of a signal value scatter point. Process 204 can be repeated for each array location, thereby generating a plurality of signal value scatter points each reflecting the levels for both alleles at each locus. The data produced in process 204 can be further analyzed by main system 101.

The number of distinct loci represented in a data set will depend on the number of individual positions in the array and on other assay conditions, for example, in the case of the GoldenGate™ assay the number of ligation probe sets utilized in the extension phase of the genotyping procedure. In theory, a multitude of different ligation probe sets, each of which corresponds to one of the 1.42 million SNPs that are estimated to be present in the human genome, are available for genotyping. In particular embodiments, one to several thousand ligation probe sets can be used. In a typical example, the number of ligation probe sets used in the extension phase can be approximately 30-50 times less than the number of positions available in an array. This permits a 30 to 50-fold redundancy in signal that is generated from each locus. This high redundancy can increase statistical confidence in the measurement of allele frequency at each locus. Thus, a method of the invention can include detection and manipulation of redundant signal values for alleles at a locus. For example, signals from redundant array locations can be averaged, summed or otherwise combined as described in WO 00/60332.

With reference to the exemplary process set out in FIG. 2, the next step in the analysis of genetic data is the outlier removal step 215 which can be performed by outlier removal module 122. Outliers are data points that are located far from the rest of the data. Given a mean and standard deviation, a statistical distribution expects data points to fall within a specific range. Data points that lie above or below a predetermined threshold, for example, outside a range of three standard deviations from the mean can be considered outliers. Another way of characterizing an outlier is to define it as a data point that emanates from a different model than do the rest of the data.

Outliers can be removed using methods based on determining the Mahalanobis distance as described, for example, in Dunagan et al., *MIT Laboratory for Computer Science*, pp. 317-318 March 2003. Outliers can also be identified as points falling outside of the median ±1.5*IQR. (where IQR is the inter-quartile range) It will be appreciated that the above-described methods exemplify some of the methods in which outliers can be detected and removed from a data set. Those skilled in the art will know or be able to determine other useful methods for outlier removal that are consistent with the systems and methods disclosed herein.

After outlier removal step 215, data normalization can be performed. There are various data normalization techniques known in the art, many of which rely on external controls. External controls are samples which are known to produce a predetermined result when analyzed. For example, an external control used in a genotyping assay can be a target DNA having a known allele frequency at one or more loci. Such controls are often included as points of reference and they do not fall within the experimental data set. As reference points, the external controls can be used to determine one or more parameters of a selected function which is used to normalize an unknown data set. The disadvantage to such methods is that it can be difficult to keep external controls constant over time. The consistency of external controls can be particularly problematic in genotyping. For example, in many genotyping formats high level multiplexing can cause variable results between copies of the same locus or even identical alleles at the same locus. In genotyping methods which utilize optical detection systems, external controls do not necessarily produce consistent interaction with the optics each time they are used. These and other problems can be ameliorated by normalizing the data using controls that are extracted from the actual data set during each genotyping run.

Accordingly, the invention provides a method of normalizing genetic data for n loci, wherein n is an integer greater than one. The method includes the steps of (a) obtaining genetic data including n sets of first and second signal values related in a coordinate system, wherein the first and second signal values are indicative of the levels of a first and second allele, respectively, at n loci; (b) identifying a set of sweep points in the coordinate system; (c) identifying a set of control points, the control points including at least a subset of the signal values that are proximal to the sweep points; (d) determining parameters of a registration transformation equation based on the set of control points; and (e) transforming the n sets of first and second signal values according to the registration transformation equation and the parameters, thereby normalizing the genetic data.

In some embodiments of the present invention, data is normalized without the use of external controls. In particular, data is normalized by selecting control points within the actual data set as a reference and then transforming the entire data set according to a registration transformation equation such that all of the data points are normalized with respect to parameters determined for the control points. As set forth in further detail below, parameters of a registration transformation equation can be determined based on the change in location for the control points once projected to set point locations on a reference line or curve. Typically, the set of control points, and thus set points, is smaller in number than the actual data set of signal value scatter points. For example, the number of control points can be at most 1%, 2%, 5%, 10%, 15%, 25% or 50% of the number of signal value scatter points. Alternatively, if desired, the methods can be carried out using a set of control points that is equivalent in number to the number of signal value scatter points.

Figure 4:
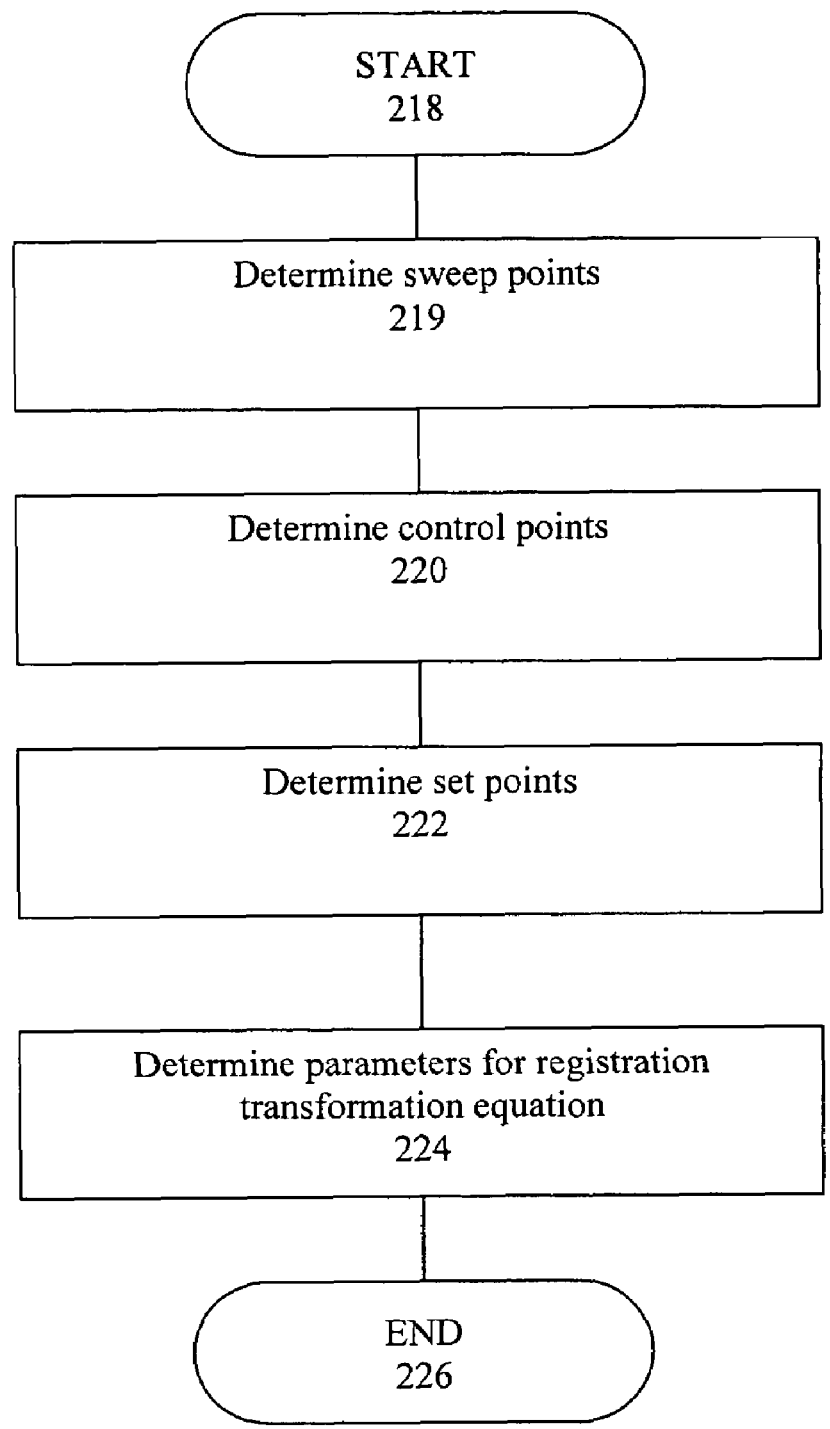
FIG. 4 is a flow diagram depicting a process of normalizing signal values.

FIG. 4 is a diagram showing the steps in normalization process 216 that can be performed by normalization module 120. The process 216 begins at start step 218 and then moves to step 219 to determine sweep points using x, y coordinate data such as the data discussed above. For purposes of explanation, the invention is exemplified herein for signal values obtained for bi-allelic loci and represented in a graphical representation having two dimensions. Those skilled in the art will understand from the disclosure herein that genetic data represented in other formats can also be used in the methods. For example, x, y coordinate data can be provided in tabular format, matrix format, or in a format used by a typical computer during data manipulation. Those skilled in the art will also recognize that similar analyses can be extended to loci having more than 2 alleles by incorporating further dimensions to the coordinate system. Thus, genetic data used in a method of the invention can include n sets of first, second and third signal values related in a coordinate system, wherein the first, second and third signal values are indicative of the levels of a first, second and third allele, respectively, at n loci.

Sweep points can be acquired by identifying a sweep reference line or sweep reference curve passing through a coordinate system and determining an upper limit for the line or curve. The upper limit can be a point on or near the sweep reference line or curve that is greater than or equal to any other signal value on or near the line or curve. However, the upper limit need not be the absolute maximum in a data set and can be, for example, a quasi-maximum point, such as, the point that occurs N points away from the absolute maximum point, or the point that occurs at the Mth percentile ranking compared to the values of all the points in the data set. Similarly, a tower limit can be identified on the sweep reference line or curve. If desired the lower limit can be the origin of the coordinate system such as zero in the case of a Cartesian coordinate system.

In particular embodiments, the sweep reference line can be an axis of the coordinate system. Sweep points can be located along both axes, if desired. In other cases it may be useful to use one or more non-axis lines that cross through the origin of a coordinate system at a desired angle. If desired, the angle of the line can be selected such that the line will cross through the expected location for a particular cluster. For example, lines that cross through the origin at a 30°, 45° or 60° angle will cross through the expected locations for the two homozygous clusters and the heterozygous cluster when bi-allelic genotyping data is plotted in a Cartesian coordinate system in which bi-allelic signal value scatter points are plotted.

A sweep of intensities between the lower and upper limits on the sweep reference curve or line can then be conducted to locate a predetermined number of sweep points falling on the line or curve. Sweep points can then be spaced along the sweep reference line or curve in a manner selected from the group consisting of linear, log-linear and non-linear. Those skilled in the art will know or be able to determine a desirable spacing based on the data distribution, for example, linear, log-linear or non-linear spacing is typically used when the distribution of signal values or signal value scatter points is linear, log-linear or non-linear, respectively.

In some embodiments, the number of sweep points is equal to three. However, the number of sweep point can be greater than 3. Increasing the number of sweep points increases the number of control points that are identified, thereby reducing the estimation error of the transformation matrix used for normalization. Thus, the number of sweep points can be at least 4, 5, 6, 7, 8, 9, 10, 20, 25, 50, 75, 100 or higher up to and including the number of signal values in the data set being analyzed.

The next step shown for process 216 is identification of control points at a step 220. The control points belong to the set of signal value scatter points that are closest to their corresponding sweep points. For example, the $3^{rd}$ control point is the signal value scatter point (in the whole set) that has the smallest distance from the $3^{rd}$ sweep point. Control points can be identified by triangulation using pairs of signal value scatter points and a sweep point. Alternatively or additionally, control points can be determined by a brute-force approach in which the distances between a sweep point and all signal value scatter points is determined and the signal value scatter point that is the shortest distance from the sweep point is identified.

In some applications, the process for determination of the closest points, if not designed carefully, can be of order $O(n^2)$ (where O is the order and n is the number of DNA samples detected), which can be very time consuming. However, the process of identifying control points can be performed using Delaunay Triangulation, which is of order $O(n)$, and, therefore relatively rapid. A Delaunay Triangulation for a set of point data can be thought of as a collection of edges which satisfy an "empty circle" property. In other words, each edge in the Delaunay Triangulation is associated with a circle which contains the edge's endpoints but no other data point. Algorithms for performing Delaunay Triangulations for sets of point data are known in the art. In one exemplary method, a Delaunay Triangulation for a set of data points is determined by first finding the set of Voronoi polygons for the data set. If an edge of a Voronoi polygon is common between two adjacent Voronoi vertices then the two adjacent Voronoi vertices are connected by a line segment. Such line segments form the collection of edges in a Delaunay Triangulation. The lengths of the Delaunay edges are then compared and the shortest edges identified, thereby determining the control points. Delaunay triangulation can be carried out, in accordance with algorithms known in the art.

After the control points are identified in step 220, set points can be determined in step 222. In this step, a set of set points is defined for the control point sets such that each set point is the location on a sweep reference line or curve where a control point is transferred. Typically, set points are approximately equally-spaced values on the sweep reference line or curve, for example, points on the axes between the fixed values of 0 and 2 such that the mean would fall on 1. It will be appreciated, however, that other choices of and spacings for set points are possible.

Once the location of the set points has been determined in step 222, the parameters of a registration transformation equation can be determined according to the change in location occurring for the control points that are projected to the set points in step 224. The transformation equation can be any of a variety of global registration methods known in the art. Global registration methods are those that apply a set of parameters to a set of data points to alter the location of the data points. The set of parameters can be derived, for example, from a subset of the data points, the entire set of datapoints, a set of control points, or a predefined function. In particular embodiments, the registration transformation equation can include an affine transformation. An Affine transformation is a linear two-dimensional geometric transformation which maps variables located at position $x_1, y_1$ into new variables $x_2, y_2$ by application of a linear combination of translation, rotation, scaling and/or shearing. The general Affine transformation is commonly written in homogenous coordinates as shown below:

$$\begin{vmatrix} x_2 \\ y_2 \end{vmatrix} = A \times \begin{vmatrix} x_1 \\ y_1 \end{vmatrix} + B$$

The Affine transformation is responsible for projecting the control points onto the set points. This makes the normalization task resemble an image registration task, which uses fiducial points. In preferred embodiments, the Affine transformation allows for 6 degrees of freedom—Xoffset, Yoffset, Xscale, Yscale, Xshear, and Yshear. After the Affine transformation, the set of projected data points becomes the set of normalized values.

In particular embodiments of the invention, the transformation step 224, in normalization process 216, includes a translation operation, rotation operation, scaling operation or shear operation or combination of two or more of these operations. Once such transformations have been performed, the scale can be modified. In other embodiments, the scale can be modified prior to the translation, rotation and/or shear modifications. One of ordinary skill in the art can readily determine appropriate orders for performing the transformation steps. In some embodiments of the present invention, not all of the steps of the transformation are performed on the data set.

A registration transformation equation used in a normalization method can include other global registration methods, such as, linear conformal transformation, projective transformation or polynomial transformation. Linear conformal transformation can include, for example, translation, rotation or scaling operations. Projective transformation is similar to affine transformation with the additional step of perspective convergence or divergence. Polynomial transformation can include a linear transformation of a given polynomial order such as orders of 2, 3 or 4 depending upon the desired fit of the transformation equation to the data being normalized.

Typically, the number of sets of control points identified in a method of the invention is equivalent to the number of dimensions in the coordinate system. For example, two sets of control points can be identified when signal values for bi-allelic loci are evaluated in a two dimensional coordinate system. For coordinate systems having more dimensions more sets of control points can be identified. For example, three sets of control points can be identified when signals for three allele loci are evaluated in a three dimensional coordinate system. Accordingly, the normalization methods can include identification of multiple sets of sweep points, control points or set points, including, for example, 2, 3, 4 or more sets. The number of sets of points can differ from the number of dimensions on a coordinate system if desired.

A method of the invention can further include a step of balancing sets of signal values by a signal transformation, thereby balancing the probability function for the distribution of the sets of signal values as a function of signal intensity. Balancing is typically carried out to make the skew of a probability density function as close as possible to zero. This usually makes the distributions more Gaussian-like, and thus opens up possibilities for simple parametric models. Balancing can be carried out to remove skew in the data or in some embodiments can be carried out to produce a normal distribution. Exemplary signal transformation methods that can be used include, for example, logarithm, arctangent, and Box-Cox signal transformations.

Once the data has been normalized, any remaining outliers can be removed. Outlier removal, which is shown in FIG. 2 as step 238, can be performed by outlier removal module 122. As described previously, various methods of outlier removal are known in the art. Once the data set has been normalized and outliers removed, each data point can still be represented by an x-coordinate and a y-coordinate. A coordinate conversion step 240 can be carried out in process 200, as diagrammed in FIG. 2. Those skilled in the art will recognize that coordinate conversion need not occur exclusively at the stage exemplified in FIG. 2. Thus, coordinate conversion can be carried out either before or after normalization and before or after outlier removal. Coordinate conversion step 240 can be performed as shown diagrammatically in FIG. 5. In step 240, Cartesian coordinates are converted to modified polar coordinates. This conversion can be performed by coordinate conversion module 124. Conversion of Cartesian coordinates to modified polar coordinates provides at least two advantages. First, it decouples the relevant information for genotyping. In other words, it decouples the position (angle) values from the magnitude (radius) values. Second, the conversion reduces the amount of heteroskedasticity in the data set. Thus, clusters that are "funnel shaped" due to higher scatter at higher signal values are converted to tighter clusters with a more symmetrical shape. Thus, data converted to modified polar coordinates can be easier to cluster than the original Cartesian coordinate data.

Figure 5:
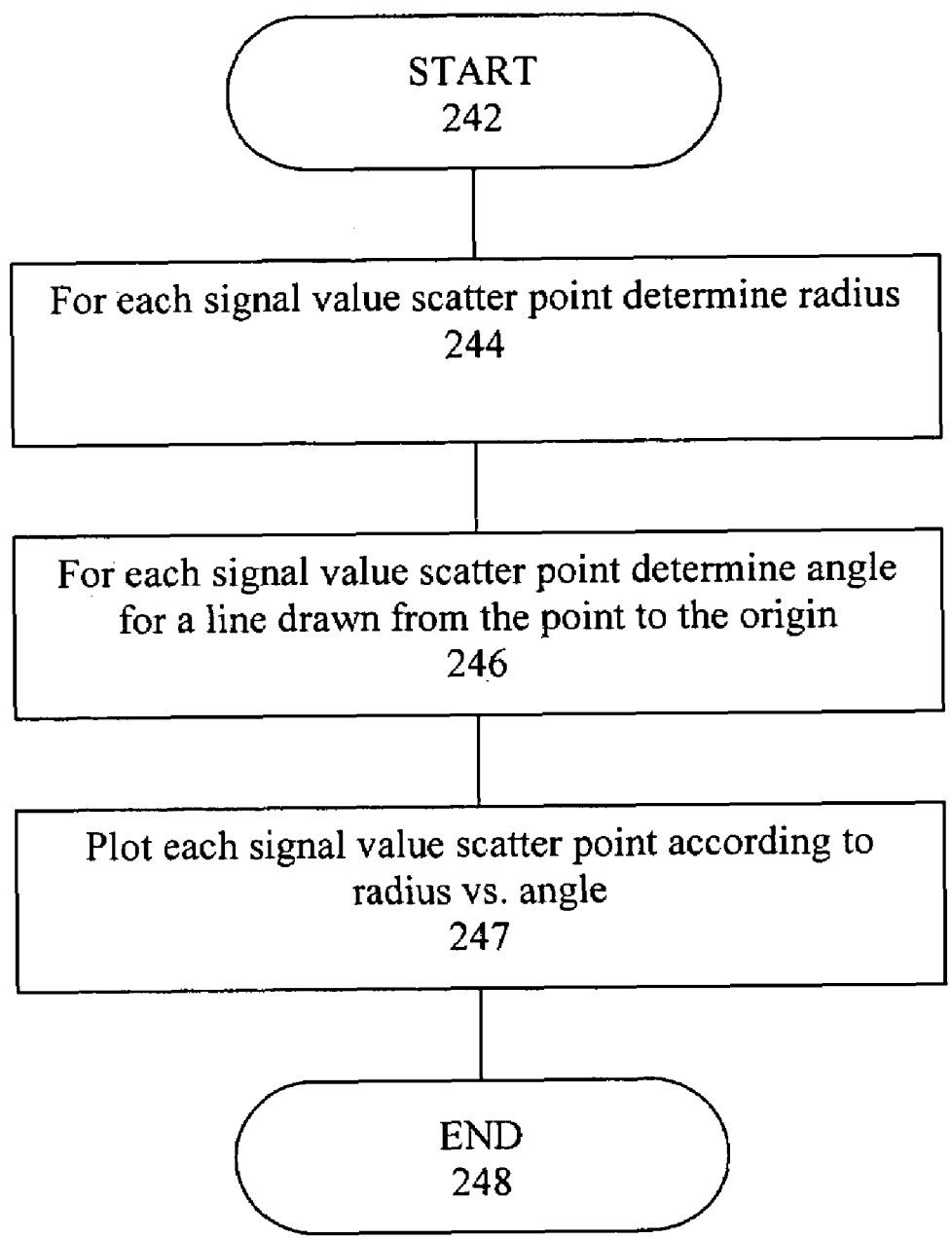
FIG. 5 is a flow diagram depicting a process of converting signal values from a Cartesian coordinate system into a modified polar coordinate system.

FIG. 5 shows that two steps can be included in modified polar coordinate conversion process 240. The process 240 begins at start step 242 and then moves to step 244 to calculate a radius (r) using the Manhattan distance according to the formula:

$$r = x + y$$

The process 240 then moves to an angle determination step 246. Angle θ can be calculated as it would be calculated in a standard conversion of Cartesian to polar coordinates. Accordingly, the following formulae are applicable:

$$\Theta = f(\alpha), \text{ wherein } \alpha = \tan^{-1} y/x$$

Other measures such as y/(y+x) can also be used in lieu of the above theta function. Process 240 can then move to step 247 in which signal value scatter points are plotted in modified polar coordinates (radius vs. angle).

It will be appreciated that steps 244 and 246 of process 240 can be performed in the order shown in FIG. 5 or vice versa.

Although the use of modified polar coordinates have been exemplified above, it will be appreciated that normal polar coordinates or other coordinate systems can also be utilized in the methods or systems disclosed herein.

For each locus, normalized data that has been converted to polar coordinates can be used to determine the locations of genotype clusters. As will be described in detail below, clusters can be defined by evaluating different cluster models with the data set and determining the fit by using parameters that are extracted from the data set to calculate a score. The model that best fits the data can be selected and, if necessary, the location of any missing clusters can be predicted based on the parameters used to obtain the best fit model. At the end of the process, a genotype profile for each locus that best fits the observed data can be reported.

In some embodiments of the present invention, the clustering and scoring processes are implemented using an artificial neural network. Thus, before describing the clustering process, features of artificial neural networks for use in clustering and score computation are described.

Artificial Neural Networks (ANN)

The systems and methods of the present invention can employ an artificial neural network to analyze cluster data. In particular embodiments, the ANN is used to analyze genetic data, such as signal values indicative of the levels of alleles in a sample to be genotyped. Generally, there are two ways in which an ANN can be implemented in an analytical system. The first method is through the use of a software-based simulator for use on a general purpose computer. An alternative method is to provide the ANN as hardware. Regardless of the implementation, there are a number of ANN architectures that have been developed and are now widely available in the art. Some ANNs require class labels or target values (that is, supervised instruction using training data) while other ANNs perform without class labels or target values (unsupervised learning). A supervised learning recursive net, unsupervised learning feedback net or feedforward net can be used in the methods and systems disclosed herein.

One commonly used ANN is a multilayer feedforward (that is, unidirectional arcs joining nodes and no cycles) net using a backpropagation of error algorithm. Typically, feedforward ANNs include an input layer of neurons, an output layer of neurons and one or more hidden layers of neurons which lie between the input and output layers. Backpropagation of error requires a teacher who knows the correct output for any input (supervised learning) and this algorithm uses gradient descent on the error to train the weights. Typically, the teacher is a human. Learning using backpropagation involves two phases. In the first phase, input parameters can be fed into the input neurons. The output neurons produce a result which may differ from the known actual result. Any difference between the known result and the output result can be used to compute an error signal for the output nodes. In the second phase, the error signal can be passed back through all nodes and weight changes made. According to the gradient descent algorithm, weights are updated proportional to the steepest gradient. Other training methods that can be used include, for example, a Levenberg-Marquardt method, or Bayesian network.

Training of an ANN can be terminated prior to the point where the network begins to memorize the training data (that is, prior to overfitting). This is one way that can be used to achieve regularization. Another method of achieving regularization that is useful in the invention is the method known in the art as early stopping. Regularization methods, for example, weight decay, are aimed at limiting the complexity on the network so that it is unable to learn peculiarities. Early stopping, at the name suggests, is a method by which training is terminated prior to memorization. Network training is often stopped (1) when the number of training cycles reaches a predetermined value; (2) when the error drops below a specific value or (3) when the slope of the gradient reaches a certain value or a specific percentage of its maximum slope during the initial decay phase (Kermani, et al. (1994) *Proceedings of the 16th Annual International Conference of the IEEE Engineering in Medicine and Biology Society* 428:2).

Figure 6:
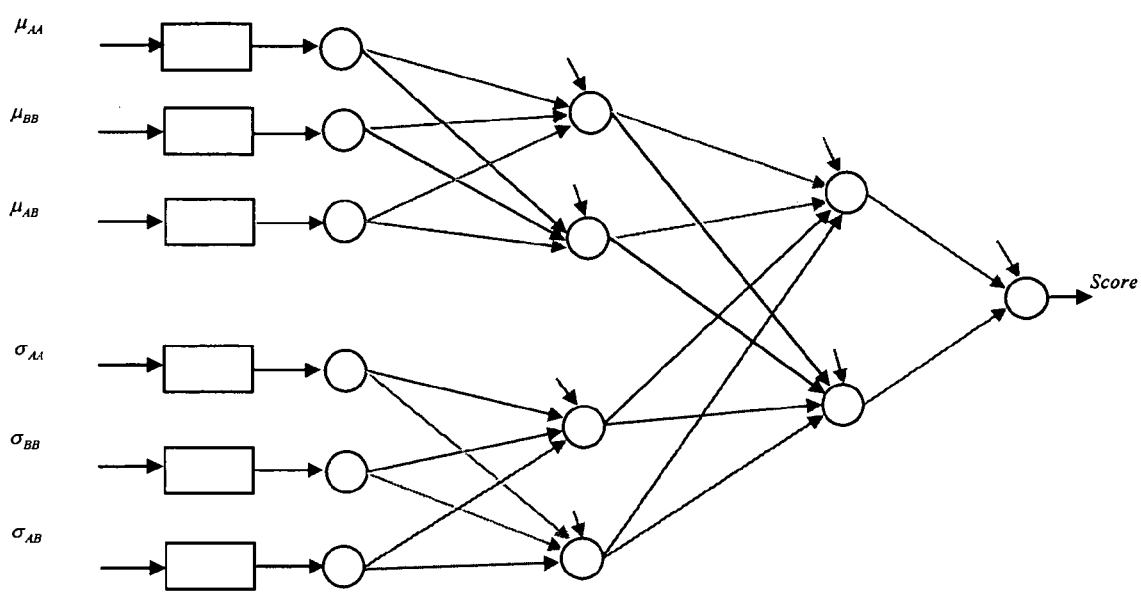
FIG. 6 is a diagram showing the architecture of a three-layer feed forward neural network useful in the analysis of cluster data.

Although other types of ANNs are available, for example radial bias networks, feedforward networks using a backpropagation of error algorithm comprise the majority of ANNs used in published and practical applications. A number of improvements have been made in backpropagation technology so as to overcome obstacles such as slow learning and problems with local minima. Some embodiments of the systems and methods described herein comprise an ANN that has the ability to analyze clustering data after a period of supervised learning which does not result in the memorization of the training data. In a preferred embodiment, the ANN is a three-layer feedforward ANN (multi-level perceptron). Regularization is performed via shared weights, weight-norm minimization and sparse connectivity. FIG. 6 displays the architecture of one embodiment of such an ANN. In FIG. 6, connections that have the same line type are constrained to have similar values throughout the training session. For the example shown in FIG. 6, layers 1 and 3 use LogSigmoidal neurons, whereas Layer 2 uses TangentSigmoidal neurons.

It will be appreciated that the exact architecture of the ANN employed in the systems and methods described herein can be modified from that exemplified above. One of ordinary skill in the art will recognize that various modifications, substitutions additions and/or deletions can be made while maintaining the ability of the ANN to perform its intended function.

In some embodiments of the present invention, an ANN which performs a clustering and/or scoring analysis is trained using an evolutionary algorithm. In a particular embodiment, the ANN is trained using a genetic algorithm; In yet another embodiment, an ANN, such as the ANN depicted in FIG. 6, is trained using a genetic algorithm. A genetic algorithm is a model of machine learning which derives its behavior from similarities with the processes of evolution on populations in nature. In a genetic algorithm, the population typically comprises chromosomes which are acted on by forces such as recombination and mutation. When a selection pressure is applied, the representation of chromosomes having desirable elements is increased in the population whereas the representation of chromosomes having undesirable elements is decreased. This process is termed selection. The parameters selected for a genetic algorithm utilized in one embodiment of the present invention are as follows:

Real Chromosomes
Number of Populations: 4
Number of Individuals per Population: 15-20
Selection Method: Stochastic Universal Sampling
Ranking Method: Linear
Selection Pressure: 1.7
Generation Gap: 0.9
Reinsertion Rate: 0.9
Recombination Method: Line Recombination
Recombination Rate: 1
Mutation Method: Real
Mutation Rate: 1
Mutation Range: 0.1
Mutation Precision: 12
Migration Interval: 20
Migration Rate: 0.1
Migration Topology: Complete Net Structure
Migration Selection: Best Individual Although an exemplary set of parameters for a genetic algorithm are provided above, those skilled in the art will appreciate that various modifications, substitutions additions and/or deletions can be made while maintaining the ability of the ANN to perform its intended function.

It will also be appreciated by one of ordinary skill in the art that other algorithms including, but not limited to, other evolutionary algorithms, such as evolutionary programming, evolution strategies, classifier systems and genetic programming, can be utilized in some embodiments of the ANNs employed in the systems and methods described herein. Further algorithms that can be used include, for example, a Levenberg-Marquardt algorithm or Bayesian algorithm.

An ANN that is employed in the systems and methods described herein can be trained in any manner consistent with its intended operation. Training is typically sufficient in duration to permit successful generalization when the ANN is tested with a test data set. Once the learning and generalization is found to be sufficient, the training can be terminated and the parameters fixed. In a genotyping context, test and training sets can easily be developed. Genotyping data can be accurately scored for several thousand loci by a single human expert. For example, consider 5 data point samples from 2000 different loci. Together there are 10,000 items to label. The human expert, however, need only label the data once. The data can then be divided into a test data set and a training set. The ANN can then be trained on the training set until learning is sufficient. At that time, the generalization can be checked using the test data set. If the generalization is successful (for example, the ANN maintains high accuracy on the test data) the training can be terminated and the parameters of the ANN fixed.

Figure 7A:
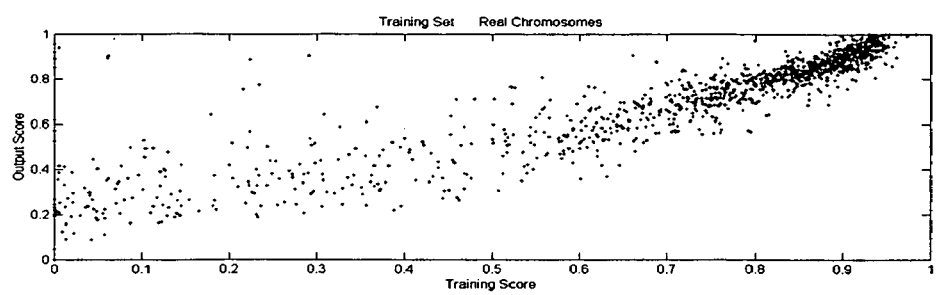
FIG. 7A is a plot of training score against output score for training data analyzed by the neural network depicted in FIG. 6.
Figure 7B:
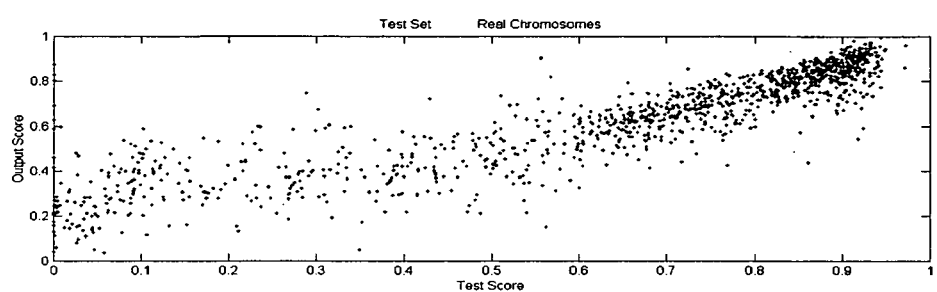
FIG. 7B is a plot of test score against output score for training data analyzed by the neural network depicted in FIG. 6.

In one embodiment of the systems and methods described herein, the ANN diagrammed in FIG. 6 was trained using the above-described genetic algorithm on data sets from 300 loci which had been scored by a human expert using visual/cognitive inspection. When tested with the test data set, successful generalization was verified as shown in FIGS. 7A and 7B.

Clustering

The invention further provides a method of clustering genetic data for n loci, wherein n is an integer greater than one. The method includes the steps of (a) obtaining genetic data including n sets of first and second signal values related in a coordinate system, wherein the first and second signal values are indicative of the levels of a first and second allele, respectively, at n loci; (b) comparing fit of the genetic data to each of a plurality of cluster models using an ANN, thereby determining a best fit cluster model; and (c) assigning the signal values to at least one cluster according to the best fit cluster model, wherein if the best fit cluster model contains at least one actual cluster and at least one missing cluster, then using a second ANN to propose a location for the at least one missing cluster. For purposes of illustration, the clustering methods are described herein in with regard to genotyping data. However, the methods can be used to cluster any data that can be plotted as scatter points.

Continuing with genotyping as an example, a normalized data set can be analyzed to determine the genotypes present at each locus. Genotypes are defined for signal values in a data set by identifying and determining data point clusters. In a two allele situation, wherein each of the two alleles is equally represented within the sample population, three clusters of data points can be present. For example, in the situation where the first allele is represented by "A" and the second allele is represented by "B," three clusters of data points corresponding to the genotypes AA, AB, and BB can be observed. In practice, however, data sets are not always divided into three distinct clusters of data points. Deviation from a 3 cluster data set can be caused by a variety of factors including, but not limited to, low frequency of one of the alleles within a population being tested, small size of a sample population being tested, positional effects arising from the location of the allele within the genome or variations in the methods used to obtain the data. Deviation from an ideal data set often times leads to substantial uncertainty regarding cluster location and even whether clusters corresponding to particular genotypes exist in the data set. If cluster locations are poorly defined, then it can become difficult to assign any new data point to a particular genotype.

Figure 8A:
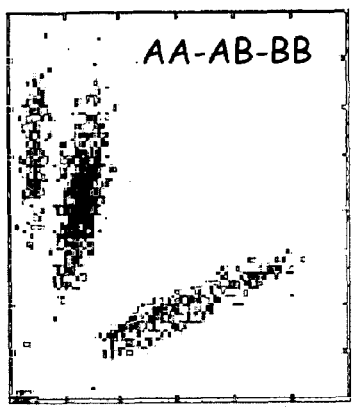
FIGS. 8A through 8G show cluster diagrams for each of seven possible clustering models for a two allele locus.
Figure 8B:
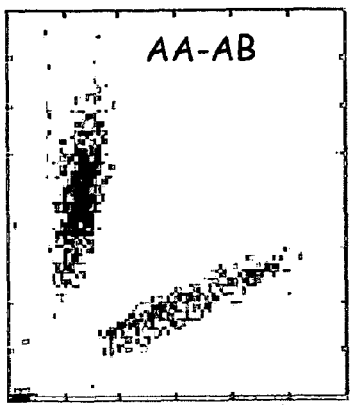
Figure 8C:
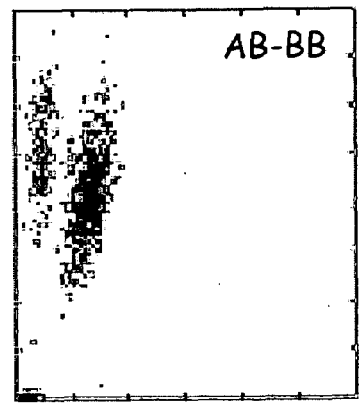
Figure 8D:
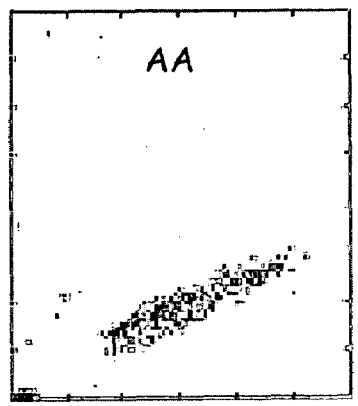
Figure 8E:
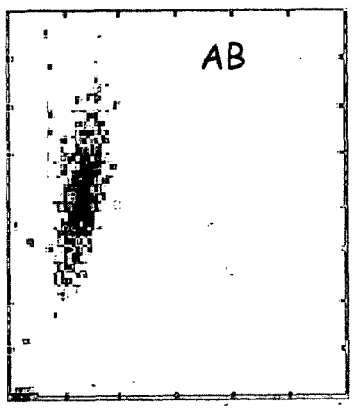
Figure 8F:
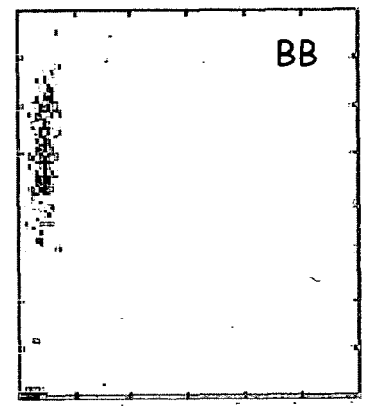
Figure 8G:
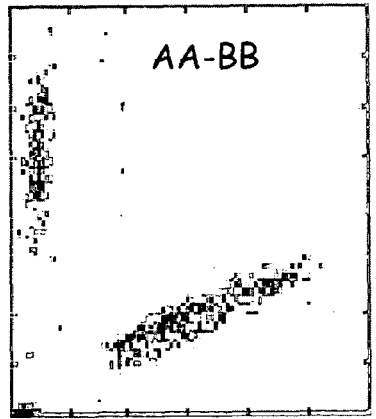

Taking for example data obtained from a two-allele locus, a first step can be determining whether all three possible genotypes are represented in the data set. If not all possible genotypes are present, a further step is to determine which of the three genotypes is/are missing. A set of data points obtained for any particular two-allele locus can potentially fit into one of seven cluster models. In the first cluster model, clusters corresponding to all three genotypes (AA, AB and BB) are present in the data set, as shown in FIG. 8A. In the next three cluster models, only two of the possible genotypes are present in the data set (that is, AA and AB, AB and BB or AA and BB) as shown in FIGS. 8B, C and D, respectively. In the final three cluster models, only one of the possible genotypes AA, AB or BB is present in the data set, as shown in FIGS. 8E, F and G, respectively. If the experimental data does not fall within the first model, the identity and location of the missing cluster can be predicted. Accordingly, a method of the invention, when used for genotyping of bi-allelic loci, can include a step of assigning signal values to at least one cluster according to the best fit cluster model, wherein if the best fit cluster model contains at least one actual cluster and fewer than three actual clusters, then using a second ANN to propose a location for at least one missing cluster, wherein the sum of actual and missing clusters is three. If the best fit cluster model contains two actual clusters, then the second ANN can be used to propose a location for one missing cluster. If the best fit cluster model contains one actual cluster, then the second ANN can be used to propose a location for two missing clusters. In the case of predicting locations for two or more missing clusters a separate ANN is trained for each missing cluster prediction.

Those skilled in the art will recognize that identification of missing clusters can be similarly carried out for data including more than 2 alleles at each locus. For example, as set forth herein previously, genotyping data used in a method of the invention can include signal values for three alleles at loci represented in a three-dimensional coordinate system. A set of data points obtained for a three-allele locus can potentially fit into one of six cluster models. Thus, a method of the invention, when used for genotyping of 3-allele loci, can include a step of assigning signal values to at least one cluster according to a best fit cluster model, wherein if the best fit cluster model contains at least one actual cluster and fewer than six actual clusters, then using a second ANN to propose a location for at least one missing cluster, wherein the sum of actual and missing clusters is six.

In some data sets, points may be so dispersed that it is difficult to define cluster locations. Without a robust analytical method, assignment of cluster locations and genotype identities is often arbitrary. In fact, many cluster determination methods that are currently known in the art rely on arbitrary or semi-arbitrary assignments of cluster boundaries to genotyping data. The systems and methods described herein provide a non-arbitrary analytical means for predicting the location of missing clusters and for assigning genotype scores. These systems and methods can utilize the normalized modified polar coordinate data sets described above and can be used for predicting the location of missing clusters and for assigning genotype scores to existing clusters using an artificial neural network.

As shown in FIG. 1, clustering module 126 can utilize ANN 132a. Useful architectures and training algorithms for ANN 132a have been described above. Accordingly, an ANN useful in the invention can include a 3 layer feed-forward ANN. Furthermore, an algorithm used for training an ANN in a method of the invention can be selected from the group consisting of a genetic algorithm, back-propagation algorithm, Levenberg-Marquardt algorithm and Bayesian algorithm.

Figure 9:
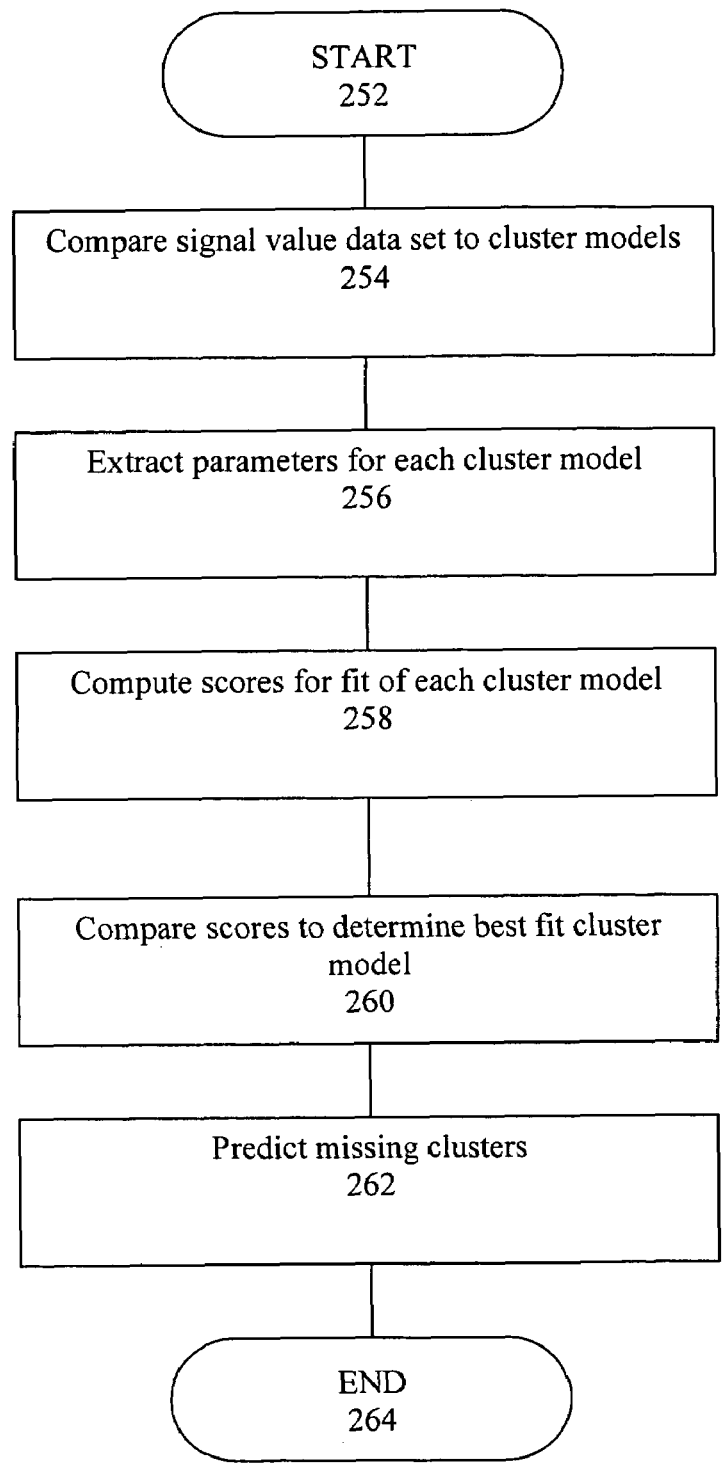
FIG. 9 is a flow diagram depicting a process of cluster analysis for genotyping data.

Further modules that can be involved in the clustering process are parameter extraction module 130 and score computation module 134. FIG. 2, which illustrates an exemplary flow of genotyping data, shows the input of normalized polar coordinate data obtained from conversion step 240 into clustering step 250. FIG. 9 illustrates a process that can be performed in clustering step 250. This process begins with cluster model comparison step 254. In a bi-alleleic genotyping example, each of the seven genotyping models described above can be superimposed on the signal value data sets generated for each locus. If the data set has been converted to a modified polar coordinate system in step 240, clusters of data points can be identified based on the probability distribution of the normalized angle values ($\theta$-values). Similarly, clusters of data points can be identified based on the probability distribution of the normalized angle values ($\theta$-values) from a data set in other coordinate systems such as a standard polar coordinate system. In particular embodiments, the distribution of $\theta$-values for each cluster can be modeled by Gaussian models. Similarly, normalized radius values (r-values) within each defined data point cluster can be fit to a Gaussian distribution model.

In parameter extraction step 256 the means ($\mu$) and standard deviations ($\sigma$) for $\theta$-values and r-values for each of the models can be extracted. For a two-allele locus, there are twelve possible parameters, which are described as follows: (1) the cluster corresponding to genotype AA includes a mean ($\mu_{AA}$) and standard deviation ($\sigma_{AA}$) for angle $\theta$ and for radius r; (2) the cluster corresponding to genotype AB includes a mean ($\mu_{AB}$) and standard deviation ($\sigma_{AB}$) for angle $\theta$ and for radius r; and (3) the cluster corresponding to genotype BB includes a mean ($\mu_{BB}$) and standard deviation ($\sigma_{BB}$) for angle $\theta$ and for radius r. Since not all of the models include all of the clusters, fewer than all of the parameters will be used in some models. For example, all twelve of the parameters are extracted for the three cluster model, eight of the parameters are extracted for the two cluster models and four of the parameters are used for the one cluster models. In one embodiment, which is shown in FIG. 1, parameter extraction step 256 can be performed by parameter extraction module 130 in connection with clustering module 126. In other embodiments, modules 126 and 130 can be fully separated. In still other embodiments modules 126 and 130 can be fully integrated.

Score computation step 258, can be performed by score computation module 134 in connection with clustering module 126 using ANN 132b. In some embodiments, a first ANN is used for predicting clusters and a second separate ANN is used for score computation. The means and standard deviations for each of the cluster models that were extracted by parameter extraction module 130 can be entered into the input neurons of ANN 132b. A score for each of the models can be produced by the output neuron. In one embodiment, which is shown in FIG. 1, score computation step 258 can be performed by score computation module 134 in connection with clustering module 126 and or parameter extraction module 130. In other embodiments, modules 126, 130 and 134 can be fully separated. In still other embodiments modules 126, 130 and 134 can be fully integrated.

As shown in step 260 of FIG. 9, after scores are computed for each of the seven models, the scores can be compared to determine which model best fits the data. If the best fitting model includes all possible genotypes, for example AA, AB and BB for bi-allelic loci, then a final score can be calculated by ANN 132b or by a separate ANN involved in final score computation. The final score can then be reported by reporting module 136 (reporting step 280 as shown in FIG. 2).

Prediction of missing cluster parameters 262 is the final step shown for process 250. This step can be performed if the best fitting model includes fewer than the expected total number of genotype clusters. To predict missing cluster parameters, ANN 132a can utilize the means and standard deviations for both the angles and radii extracted from signal value clusters that are present in a data set. Once parameters for missing clusters are predicted, ANN 132 or a separate score computation ANN, can use the parameters to identify the cluster to which particular signal values belong. If a second missing cluster location is to be predicted, a second ANN can utilize the means and standard deviations for both the angles and radii extracted from signal value clusters to determine parameters for the second missing cluster.

Those skilled in the art will recognize that the ANNs described above for comparing fit of genetic data to cluster models and for identifying missing clusters can be used independently of each other. Accordingly the invention provides a method of clustering data, the method including the steps of (a) comparing fit of a set of data points to each of a plurality of cluster models using an artificial neural network, thereby determining a best fit cluster model; and (c) assigning the data points to at least one cluster according to the best fit cluster model.

Also provided is a method of clustering data, the method including the steps of (a) comparing fit of a set of data points to each of a plurality of cluster models, thereby determining a best fit cluster model; and (b) assigning the data points to at least one cluster according to the best fit cluster model, wherein if the best fit cluster model contains at least one actual cluster and at least one missing cluster, then using a second artificial neural network to propose a location for the at least one missing cluster.

In the case of genotyping, missing cluster parameters and locations for datapoints can be used to generate a final genotyping score (step 270) such that signal values are assigned to particular output clusters. As shown in process 200 (FIG. 2) this score can be reported in step 280 by reporting module 136. Accordingly, the invention provides a method of providing information to a user, wherein the information is obtained from a method set forth herein previously. Exemplary information includes, without limitation, a genotyping score, a listing or plot of signal values, or a listing or plot of normalized signal values. Information provided to a user can be displayed on a graphical user interface, provided in hardcopy form or stored in a computer readable memory. The information can be transmitted via a computer network such as the worldwide web.

Although the systems and methods for the analysis of cluster data have been described with respect to a particular ANN, one of ordinary skill in the art will recognize that a number of modifications, substitutions additions and/or deletions can be made while retaining operability of the described systems and methods.

EXAMPLE I

Normalizing Genotyping Data

This example demonstrates a method for normalizing genotyping data using a transformation equation that includes a translation operation, rotation operation, shear operation and scale operation.

Figure 10A:
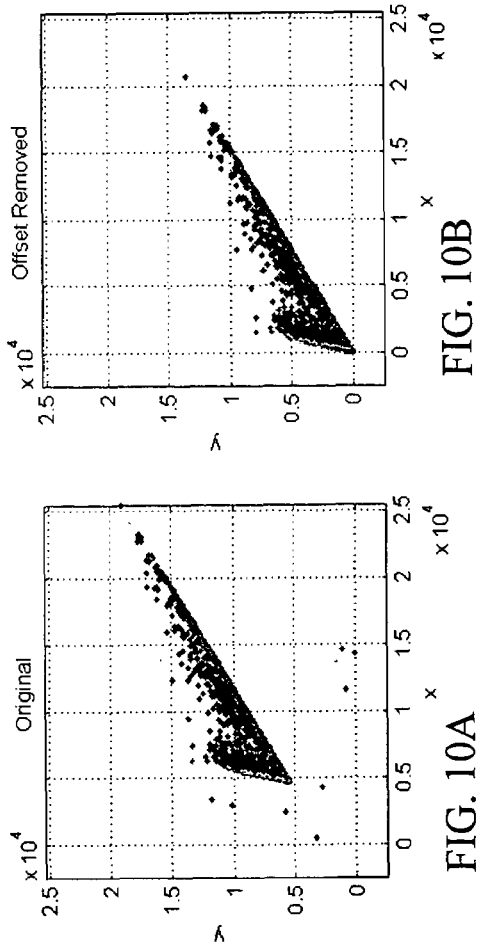
FIGS. 10A through 10F show plots of data transformation resulting from various stages of normalization.

FIG. 10A shows a plot of signal value scatter points typical of a GoldenGate™ based genotyping assay. The x axis of the plot represents intensity of signals from probes for A alleles and the y axis represents intensities of signals from probes for B alleles. Each point is plotted according to intensity of signals for an A allele and B allele measured at a particular array location.

In a first step outliers were identified and removed based on statistics on intensity. In particular, sum of intensities of the points that fell into the lower quartile were removed. Outliers were also removed based on missing values.

Figure 10B:
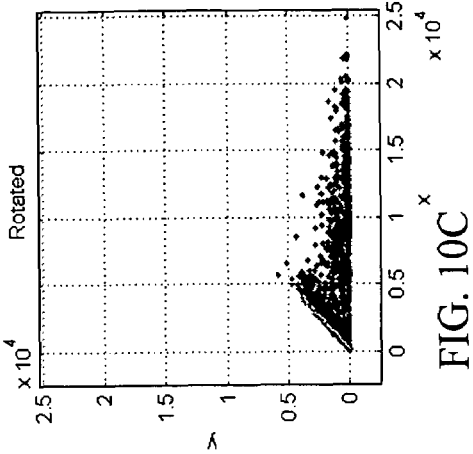

After outlier removal, the signal value scatter points were translated as follows. An X-sweep was carried out such that sweep points spaced along the x axis were identified and individual scatter points that were closest to each sweep point was identified by Delaunay triangulation. The scatter points that were closest to each x axis sweep point were defined as candidate homozygote A control points (dark grey points in FIG. 10A). Using a similar sweep on the y axis candidate homozygote B control points were identified (light grey points in FIG. 10A). A first straight line was then fit through the candidate homozygote A control points and a second straight line was fit through the candidate homozygote B control points. The intercept of the two lines was computed. This intercept identified the amount of shift (translation) in the x and y directions for the control points thus establishing parameters for translation. A translation operation was then performed on all the signal value scatter points, using the identified parameters, resulting in the plot of FIG. 10B.

Figure 10C:
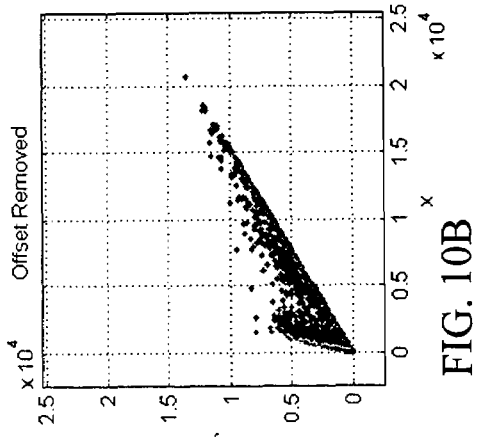

Following translation, the signal value scatter points were rotated as follows. An X-sweep was carried out on the translated signal value scatter points, and via triangulation, further candidate homozygote A control points were identified. These control points were added to the candidate homozygote A control points that were identified during the translation transformation, thereby creating a combined set of candidate homozygote A control points (dark grey points in FIG. 10B). A straight line was then fit to the combined set of candidate homozygote A control points. The angle between this line and the X-axis defined the amount of rotation in the data. Based on this value, a rotation matrix was performed on the complete set of translated signal value scatter points. The resulting translated and rotated data is shown in FIG. 10C.

Figure 10D:
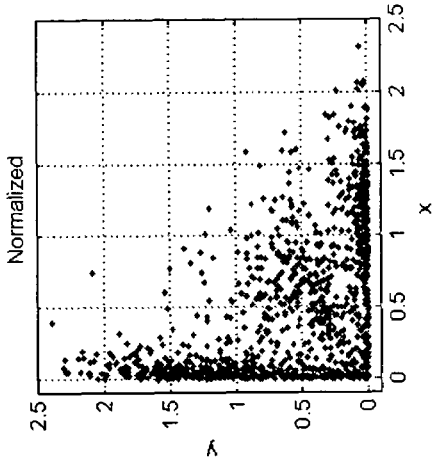

Following rotation, the signal value scatter points were shear translated as follow. A Y-sweep was carried out, and further candidate homozygote B control points were identified, by triangulation. These control points were added to the previously found candidate homozygote B control points to form a combined set of candidate homozygote B control points (light grey points in FIG. 10C). A straight line was fit to the combined set of candidate homozygote B control points. The angle of the line identified the shear parameter, which was used in a shear correction matrix applied to the complete set of translated and rotated signal value scatter points. The resulting plot is shown in FIG. 10D.

Figure 10E:
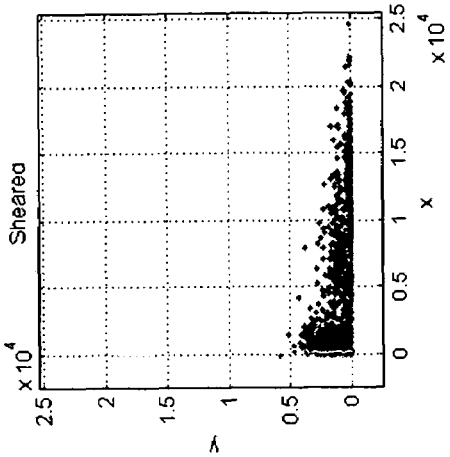

Next a scaling transformation was performed on the translated, rotated and sheared data. An X-sweep was carried out, and further candidate homozygote B control points were identified, by triangulation. These control points were added to the previously found candidate homozygote B control points to form a combined set of candidate homozygote B control points (dark grey points in FIG. 10D). A statistical robust measure of the range of the combined set of candidate homozygote B control points was used to define an x scaling parameter. The complete set of translated, rotated and sheared signal value scatter points was divided by the x scaling parameter. By a similar transformation the set of candidate homozygote A control points was used to define a y scaling parameter and complete set of translated, rotated, sheared, and x-scaled signal value scatter points was divided by the y scaling parameter. The resulting plot is shown in FIG. 10E.

Figure 10F:
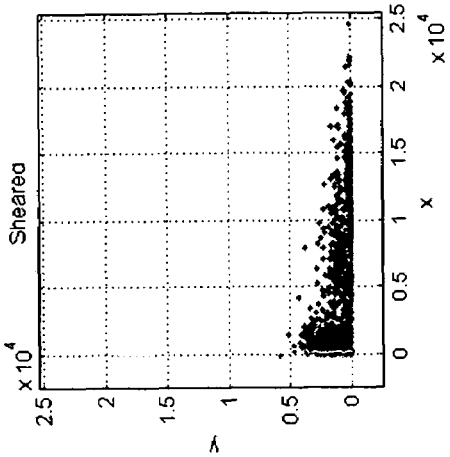

The normalized genotyping data resulting from the above operations is depicted in FIG. 10F.

EXAMPLE II

Clustering Genotyping Data

This example demonstrates a method for clustering genotyping data into one or more groups.

If the data is to be grouped into one cluster, all the points are associated to that one cluster.

For the case of two clusters, genotyping data is plotted in polar coordinates. The following steps are carried out in the Theta dimension. A moving cut-off point is tested at pre-defined intervals. At each cut-off point, the points to the left of the cut-off are assigned as one cluster, and the points to the right are assigned to the other cluster. Statistics of the two clusters are extracted. Two energy functions are computed. The first one is the negative log likelihood of the data to the model. The second one is the sum of standard deviations of the present data clusters. The two energy functions are combined into a single energy function. After evaluating all the possible cut-offs from among the tested moving cut-off points, the cut-off that renders the lowest energy function is picked.

For the case of three clusters, the process is similar to the two cluster case, with the following modifications. Two moving cut-offs are tested. Accordingly, two additional energy functions are computed. One of the additional energy functions quantitates and evaluates the distance between expected locations of clusters and their present locations. The other additional energy function has to do with the excess metric which has to do with Hardy-Weinberg equilibrium, with the difference that only the excess heterozygote scenario is penalized. This second energy function is based on the following algorithm:

Score is 1−max(0, estimate of 2 pq minus 2*estimate of p*estimate of q).

$n = aa.n + ab.n + bb.n;$ $phat = \max(.1, sqrt(aa.n./n));$ $qhat = \max(.1, sqrt(bb.n./n));$ two$pqhat = \max(.09, ab.n/n);$ $het\text{excess} = \max(0, two pqhat - 2*phat*qhat);$ score = 1 − $het$excess;

Throughout this application various publications, patents or patent applications have been referenced. The disclosures of these publications in their entireties are hereby incorporated by reference in this application in order to more fully describe the state of the art to which this invention pertains.

The term "comprising" is intended herein to be open-ended, including not only the recited elements, but further encompassing any additional elements.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit and scope of that which is described and claimed.

What is claimed is:

1. A method of genetic analysis, comprising carrying out instructions on a computer system for
    (a) obtaining genetic data comprising n sets of first and second signal values related in a coordinate system, wherein said first and second signal values are indicative of the levels of a first and second allele, respectively, at n loci, wherein n is an integer greater than one;
    (b) comparing fit of said genetic data to each of a plurality of cluster models using an artificial neural network, thereby determining a best fit cluster model;
    (c) assigning said signal values to at least one cluster according to said best fit cluster model, wherein if said best fit cluster model contains at least one actual cluster and at least one missing cluster;
    (d) using a second artificial neural network to create a proposed location for said at least one missing cluster; and
    (e) analyzing genetic data using said cluster model, wherein said analyzing is performed for determining a genotype based on said genetic data.

2. The method of claim 1, wherein said plurality of cluster models comprises at least seven cluster models.

3. The method of claim 1, further comprising training said first or second artificial neural network with an algorithm selected from the group consisting of a genetic algorithm, back-propagation algorithm, Levenberg-Marquardt algorithm and Bayesian algorithm.

4. The method of claim 1, wherein said first or second artificial neural network comprises a 3 layer feed-forward artificial neural network or a two layer artificial neural network.

5. The method of claim 1, wherein said coordinate system comprises two dimensions.

6. A method of genetic analysis, comprising carrying out instructions on a computer system for
    (a) obtaining genetic data comprising n sets of first and second signal values related in a coordinate system, wherein said first and second signal values are indicative of the levels of a first and second allele, respectively, at n loci, wherein n is an integer greater than one;
    (b) comparing fit of said genetic data to each of a plurality of cluster models using an artificial neural network, thereby determining a best fit cluster model;
    (c) assigning said signal values to at least one cluster according to said best fit cluster model, wherein if said best fit cluster model contains at least one actual cluster and fewer than three actual clusters;
    (d) using a second artificial neural network to create a proposed location for at least one missing cluster, wherein the sum of actual and missing clusters is three; and
    (e) analyzing genetic data using said cluster model, wherein said analyzing is performed for determining a genotype based on said genetic data.

7. The method of claim 6, wherein if said best fit cluster model contains one actual cluster, then using said second artificial neural network to propose a location for two missing clusters.

8. The method of claim 7, further comprising separately training said artificial neural network for proposing locations for said two missing clusters.

9. The method of claim 6, wherein if said best fit cluster model contains two actual clusters, then using said second artificial neural network to propose a location for one missing clusters.

10. The method of claim 6, wherein said genetic data comprises n sets of first, second and third signal values related in a coordinate system, wherein said first, second and third signal values are indicative of the levels of a first, second and third allele, respectively, at n loci.

11. The method of claim 10, wherein said coordinate system comprises three dimensions.

12. The method of claim 11, wherein wherein if said best fit cluster model contains at least one actual cluster and fewer than six actual clusters, then using a second artificial neural network to create a proposed location for at least one missing cluster, wherein the sum of actual and missing clusters is six.

13. The method of claim 1, wherein said genetic data is represented in a graphical format.

14. The method of claim 13, wherein said graphical format comprises Cartesian coordinates.

15. The method of claim 1, wherein said genetic data is provided in a tabular format.

16. The method of claim 1, further comprising reporting said best fit cluster model to a user.

17. The method of claim 1, wherein said genetic data comprises data from a genotyping assay.

18. The method of claim 17, further comprising generating a genotyping score from said best fit cluster model.

19. A method of genotyping, comprising carrying out instruction on a computer system for
   (a) obtaining genetic data comprising n sets of first and second signal values related in a coordinate system, wherein said first and second signal values are indicative of the levels of a first and second allele, respectively, at n loci, wherein n is an integer greater than one;
   (b) comparing fit of said genetic data to each of a plurality of cluster models using an artificial neural network, thereby determining a best fit cluster model;
   (c) assigning said signal values to at least one cluster according to said best fit cluster model, wherein said best fit cluster model contains at least one actual cluster and at least one missing cluster;
   (d) using a second artificial neural network to create a proposed location for said at least one missing cluster; and
   (e) generating a genotyping score from a genetic analysis using said best fit cluster model, wherein said genotyping score is used to determine a genotype.

20. The method of claim 19, further comprising reporting said genotyping score to a user.

* * * * *

UNITED STATES PATENT AND TRADEMARK OFFICE
CERTIFICATE OF CORRECTION

PATENT NO. : 7,467,117 B2 Page 1 of 1
APPLICATION NO. : 11/270227
DATED : December 16, 2008
INVENTOR(S) : Bahram Ghaffarzadeh Kermani It is certified that error appears in the above-identified patent and that said Letters Patent is hereby corrected as shown below:

Column 24, line 13 (claim 1), "wherein if said" should be changed to --wherein said--

Column 24, line 47 (claim 6), "wherein if said" should be changed to --wherein said--

Column 24, line 67 (claim 9), "clusters" should be changed to --cluster--

Column 25, line 8 (claim 12), "wherein wherein" should be changed to --wherein--

Column 26, line 2 (claim 19), "instruction" should be changed to --instructions--

Signed and Sealed this

Twenty-first Day of July, 2009

JOHN DOLL
*Acting Director of the United States Patent and Trademark Office*